(12) United States Patent
Alzaga et al.

(10) Patent No.: US 11,969,168 B2
(45) Date of Patent: Apr. 30, 2024

(54) SURGICAL STAPLE HAVING TWO MOVABLE ARMS CONNECTED BY A TRANSVERSE CONNECTION AREA

(71) Applicant: INSTITUT HOSPITALO-UNIVERSITAIRE DE CHIRURGIE MINI-INVASIVE GUIDEE PAR L'IMAGE, Strasbourg (FR)

(72) Inventors: Amilcar Alzaga, Mexico City (MX); Peter Halvax, Pecs (HU); Lee L. Swanstrom, Portland, OR (US)

(73) Assignee: INSTITUT HOSPITALO-UNIVERSITAIRE DE CHIRURGIE MINI-INVASIVE GUIDEE PAR L'IMAGE, Strasbourg (FR)

( * ) Notice: Subject to any disclaimer, the term of this patent is extended or adjusted under 35 U.S.C. 154(b) by 547 days.

(21) Appl. No.: 17/101,183

(22) Filed: Nov. 23, 2020

(65) Prior Publication Data
US 2021/0068821 A1 Mar. 11, 2021

Related U.S. Application Data

(63) Continuation of application No. 15/549,517, filed as application No. PCT/FR2016/050328 on Feb. 12, 2016, now Pat. No. 10,842,484.

(30) Foreign Application Priority Data

Feb. 13, 2015 (FR) ...................................... 1551195

(51) Int. Cl.
*A61B 17/064* (2006.01)
*A61B 17/00* (2006.01)
*A61B 17/068* (2006.01)

(52) U.S. Cl.
CPC .... *A61B 17/0644* (2013.01); *A61B 17/00234* (2013.01); *A61B 17/0684* (2013.01); *A61B 2017/00526* (2013.01)

(58) Field of Classification Search
CPC ..... A61B 17/00; A61B 17/064; A61B 17/068; A61B 17/0644; A61B 17/0684;
(Continued)

(56) References Cited

U.S. PATENT DOCUMENTS

| 1,123,290 A | 1/1914 | Von Herff |
| 1,728,316 A | 9/1929 | VanWachenfeldt |

(Continued)

FOREIGN PATENT DOCUMENTS

WO  WO-02/019920 A1  3/2002

OTHER PUBLICATIONS

U.S. Appl. No. 15/549,517, filed Aug. 8, 2017, Amilcar Alzaga Peter Halvax Lee L. Swanstrom.

*Primary Examiner* — Vi X Nguyen
(74) *Attorney, Agent, or Firm* — Harness Dickey & Pierce, PLC (57) ABSTRACT

A surgical staple has two movable arms connected by a transverse connection area. Each one of the arms has a pinching area and a fastening end and the transverse connection area is deformable to allow the movable arms to be moved together by bending around the axis of the transverse connection area.

21 Claims, 10 Drawing Sheets

(58) Field of Classification Search
CPC .... A61B 17/00234; A61B 2017/00526; A61B 17/08; A61B 2017/00004
See application file for complete search history.

(56) References Cited

U.S. PATENT DOCUMENTS

| | | | |
|---|---|---|---|
| 2,232,142 A | | 2/1941 | Seymour |
| 2,254,620 A | | 9/1941 | Miller |
| 2,684,070 A | | 7/1954 | Kelsey |
| 4,317,451 A | | 3/1982 | Cerwin |
| 4,610,251 A | | 9/1986 | Kumar |
| 4,683,895 A | | 8/1987 | Pohndorf |
| 5,236,440 A | | 8/1993 | Hlavacek |
| 5,395,030 A | * | 3/1995 | Kuramoto .......... A61B 17/1152 227/19 |
| 5,683,405 A | | 11/1997 | Yacoubian |
| 6,616,686 B2 | | 9/2003 | Coleman |
| 7,887,563 B2 | | 2/2011 | Cummins |
| 9,517,064 B2 | | 12/2016 | Sarradon |
| 2008/0173693 A1 | | 7/2008 | Mas et al. |
| 2008/0177300 A1 | | 7/2008 | Mas |
| 2008/0249566 A1 | | 10/2008 | Harris |
| 2008/0262541 A1 | | 10/2008 | Sater |
| 2008/0269803 A1 | | 10/2008 | Sater |
| 2009/0242609 A1 | | 10/2009 | Kanner |
| 2009/0264923 A1 | | 10/2009 | Sater |
| 2009/0272786 A1 | * | 11/2009 | Zeiner .................. A61B 17/068 227/176.1 |
| 2011/0144691 A1 | | 6/2011 | Cummins |
| 2013/0006271 A1 | | 1/2013 | Vold |
| 2015/0133969 A1 | | 5/2015 | Gupta |

\* cited by examiner

SURGICAL STAPLE HAVING TWO MOVABLE ARMS CONNECTED BY A TRANSVERSE CONNECTION AREA

CROSS-REFERENCE TO RELATED APPLICATIONS

This application is a Continuation of U.S. patent application Ser. No. 15/549,517 filed Aug. 8, 2017, now U.S. Pat. No. 10,842,484, which is a National Phase entry of International Application No. PCT/FR2016/050328 filed on Feb. 12, 2016, and which claims priority to French Patent Application Serial No. 15/51195 filed on Feb. 13, 2015, all of which are incorporated by reference herein.

TECHNICAL FIELD

The present invention relates to the field of endoscope surgery and more precisely staples for internal suturing and ligature as well as the placing of implants fixed to tissue by staples. Metal staples (usually made from stainless steel) are used in endoscopic or laparoscopic surgery to hold the two tissue lips in contact or for fixing a prosthesis such as a stent. They must have a size in the deployed position compatible with passage through the endoscope tube and are manipulated by an applicator placed at the end of the endoscope tube. Unlike staples intended for cutaneous, bone or ocular application, endoscopic staples must allow positioning and closure in a very small space with a small possibility of movement.

BACKGROUND

In the prior art various solutions intended for endoscopic placing are known. U.S. Patent Publication No. 2011/0144691 proposes a staple in the general form of a U with a base extended by two legs in the form of an L. The legs are folded in order to form an angle of approximately 90°. They have a pointed portion perforating the tissues. They also have compression structures placed above the perforation portion limiting the depth and penetration of the perforation portion.

U.S. Pat. No. 4,610,251 describes an external stable intended to join the two edges of an incision in the skin of a patient. These staples are intended to be used in an applicator and have two arms with bifurcated ends piercing the skin at two different angles. The international patent application WO 0219920 describes an intracorporeal staple having a base extended by two lengths penetrating the tissues. The base can be deformed in order to close the staple on a wound.

U.S. Pat. No. 2,684,070 describes a staple formed by a rigid wire deformed so as to have an elongate central part extended by pointed parts. U.S. Patent Publication No. 2008/0173693 describing an applicator for placing staples is also known.

The solutions of the prior art relating to external staples intended to close skin wounds are not fully suited to endoscopic application. For endoscopic applications, the staple must have a very small size, with structures with a maximum thickness of less than one millimetre and a length of a few millimetres. Moreover, the staples of the prior art involve perforation of the tissue lips, thus causing the initiation or a tear. All the staples proposed in the prior art have points penetrating deeply into the tissues in order to ensure holding thereof, which causes lesions to the cell material and sources of infection. Finally, the pressure exerted on the tissues by the staples of the prior art during and after closure is poorly controlled and may cause damage or even local necrosis.

SUMMARY

The present invention aims to remedy these drawbacks by proposing a staple for endoscopic application, making it possible to manipulate and fix the tissues and/or implants in a more suitable manner in a small space accessible endoscopically. To this end, the invention relates, according to its most general acceptance, a surgical staple having two arms connected by a transverse connection area characterised in that each of said arms has a gripping area and also an attachment end, and in that said transverse connection area is deformable to enable said movable arms to be brought closer together by folding about a central part of said transverse connection area.

The staple according to the invention has two arms able to move with respect to each other, each of the two arms having two curved extensions:
  one of the extensions has a pointed end in order to provide superficial penetration of the tissue with a view to being brought closer before clamping thereof. The longitudinal axis of this extension preferably forms an angle of 45°±30° with respect the plane perpendicular to the symmetry axis of the staple, passing through the tapered ends of the two arms, so as to fit flush with the surface of the edge of the tissue and to penetrate not perpendicularly to the surface of the tissues but at an angle favouring dragging of the edges of the tissues in order to bring the two edges together when the arms are bent towards each other;
  the other extension has a flat for providing, in combination with the flat on the extension of the opposite arm, gripping without perforation of the two edges of tissues to be held.

These two flats are configured so as to have flattened gripping surfaces gripping the two lips of tissues joined when the two arms are brought together in the position of holding the tissues.

At the moment of application, the staple is open, that is say to the arms are separated, with an angle that may range from 180° (the two arms are then aligned on either side of the connection area) to approximately 90°. They are applied in this open position to the area to be treated, so that the pointed ends penetrate superficially in the edges of the tissue to be brought together. Next, the staple is deformed in order to bring together the arms, the tapered extensions of which have superficially hooked onto the two lips of the tissues, which produces the dragging of the edges of the tissues by the two tapered extensions until the edges join and are "gripped" between the flats of the two flat ends.

To allow introduction by an endoscopic tube with a minimal cross section, the two arms are initially aligned. The two gripping surfaces of the flats form the gripping areas consisting of the semi-cylindrical surfaces. The tangents of each of the semi-cylindrical surfaces, at the central point of the gripping area on the tissues when the staple is closed, form between them an angle of less than 30°. These tangents may be parallel, convergent or divergent. The radius of curvature of these semi-cylindrical surfaces is greater than 10° of the length of the arm, and may be infinite when the gripping surface is planar. The radius of curvature of each semi-cylindrical surface is greater than 10° of the length of an arm.

To bring together the two arms, a mechanical deformation is exerted, causing the folding of the arms with respect to a single axis contained in the symmetry plane of the staple and passing through the junction area of the two arms. Preferably, said arms are arched.

According to a first variant embodiment, said transverse connection area has a semi-tubular form and said arms are movable, by deformation of said transverse connection area, between an idle position in which they are coplanar and opposed symmetrically with respect to a midplane passing through the axis of said semi-tubular transverse area, and a position where they are folded towards each other. Advantageously, each of the arms has a pointed attachment end forming a pointed hook extending in front of the plane comprising the arm and the axis of said semi-tubular transverse area. Preferably, the tangent of said pointed attachment ends forms an angle of between 0° and 70°, preferably between 15° and 60°, with respect to the plane comprising the arm and the axis of said transverse area.

According to a particular embodiment, each of the arms has a shoulder defining a gripping surface configured so that said gripping surfaces come into contact with the external surfaces of the tissue area to be fixed, when the staple is closed. Advantageously, said shoulder is formed by an elastically deformable arched lug, one end of which is connected to one of said arms and the other end forming said gripping surface.

According to a second embodiment, each of the arms has a forked end formed by an attachment end and a curved lug having a gripping surface, said arms being movable, by deformation of said transverse connection area, between an idle position in which they are substantially aligned and opposed symmetrically with respect to a midplane passing through the axis of said semi-tubular transverse area, and a position in which they are folded towards each other. According to a first variant, the distance between the pointed ends is greater than the distance between the gripping surfaces when the staple is closed. According to a second variant, the distance between the pointed ends is less than the distance between the gripping surfaces when the staple is closed.

The invention also relates to an applicator for a surgical staple according to at least one of the preceding claims, said applicator having at least one tubular element with a cross section corresponding substantially to the transverse envelope of the staple, the applicator comprising a movable member having a means for temporary cooperation with the transverse connection area of the staple in order to move the staple relative to said tubular element and means for providing the deformation of the legs of the staple, characterised in that the interaction between said cooperation means and the transverse connection area is achieved on the internal surface of the transverse connection area, and in that the deformation of the staple is achieved by the interaction between the external surface of the legs and the front end of said tubular element. According to a first variant, the staple is placed in the longitudinal position in a tubular extension, and articulated so as to tilt when extracted out of this tubular extension. According to a second variant, the staple is placed in the transverse position, and driven by a lug secured to a longitudinally movable rod against the front surface of a tubular sleeve.

The invention also relates to a method for manufacturing a staple, characterised in that a configuration having two movable arms connected by a transverse connection area is cut from a metal sheet, each of said arms having a gripping area and an attachment end and in that said transverse connection area is deformable so as to enable said movable arms to be brought together by folding around the axis of said transverse connection area. Advantageously, said cutting is carried out with a tool (in particular a laser beam or a water jet) inclined in a constant manner during the cutting path, with an angle of between 10° and 55°.

BRIEF DESCRIPTION OF THE DRAWINGS

The invention will be understood better from a reading of the following description, referring to the accompanying drawings corresponding to non-limitative example embodiments, where.

DETAILED DESCRIPTION

Detailed Description of a First Example Embodiment of a Staple

Figure 1:
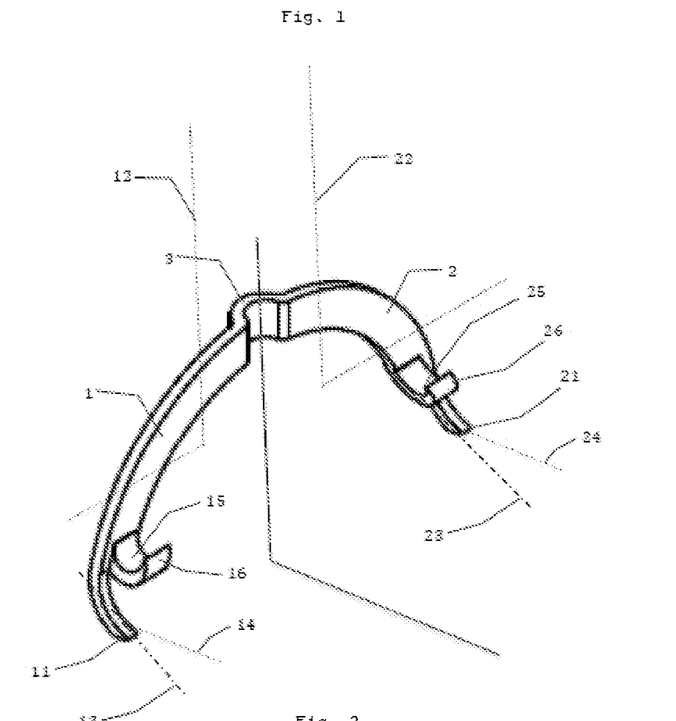
FIG. 1 shows a perspective view of a staple according to a first variant embodiment of the invention.
Figure 2:
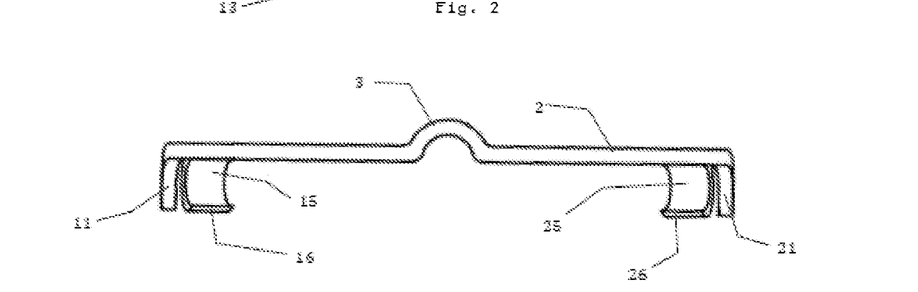
FIG. 2 shows a plan view of this staple in the open position.
Figure 3:
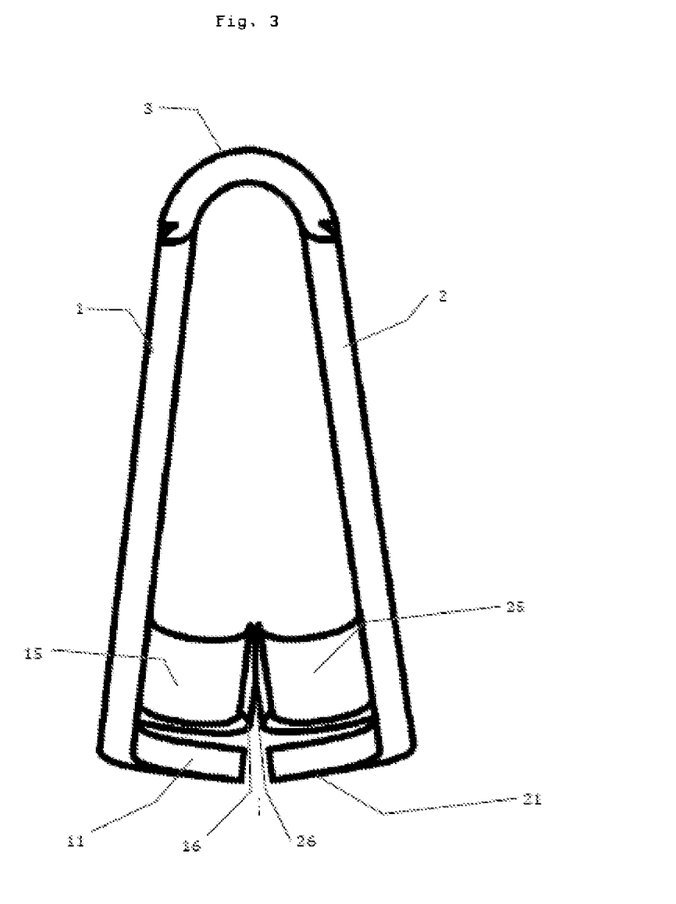
FIG. 3 shows a plan view of this staple in the closed position.

FIGS. 1 to 3 show views of a first example embodiment of a staple according to the invention. The staple has, in front view, a roughly semi-annular or "horseshoe" form. In the example described, the staple is formed by cutting steel or titanium but may also be formed by shaping a metal wire or biodegradable material. In this preferred example, the material is rigid and deformable with low elasticity and without shape memory, so as to preserve the shape imposed during deformation for bringing together the arms.

It has two arched arms (1, 2) extending symmetrically with respect to a midplane (3) passing through the middle of a connection portion (3). The middle portion (3) designates simply the part lying between the two arms (1, 2). There is no separation between this area referred to as the connection portion (3) and the arms (1, 2) in the example described. However, in other embodiments, it can be envisaged providing an area (3) connected to the arms (1, 2) by hinges or folding lines.

This middle portion (3) has a semi-tubular shape and is produced by rearward deformation of the material with a cylindrical die. The semi-tubular form of the middle portion (3) allows positioning of a guide member provided at the end of an endoscope instrument, in order to facilitate manipulation of the staple at the time of its fitting. Each of the two arms (1, 2) has a pointed end (11, 21) in the form of a hook, extending in front of the transverse plane (12, 22) containing the corresponding arm (1, 2).

The tangent (13, 23) to the pointed end (11, 21) forms, with respect to the normal (14, 24) to the transverse plane (12, 22), an angle greater than 0° and less than 90°, and preferably between 5° and 50°. This pointed end makes it possible to hook onto the tissues in the vicinity of the area where the staple is placed, and to exert a lateral traction to bring them together before stapling. When the angle formed by the tangent is large, dragging the tissues without perforating them is favoured. If the angle is smaller, penetration of the pointed end into the tissues is favoured.

The two arms (1, 2) also each carry a hook (15, 25) projected in front of the transverse plane (12, 22), and positioned closer to the pointed end (11, 21) than the transverse connection area (3). The pointed attachment end (11, 21) and the hook (15, 25) can be produced so as to form a split end of the arm (1, 2), one of the tongues of this split end forming the attachment point (11, 21) and the other forming the hook (15, 25).

In the example described, the uncoiled length of the attachment point (11, 21) is substantially equal to the uncoiled length of the hook (15, 25). This hook (15, 25) has a gripping surface (16, 26) parallel to the transverse plane (12, 22). This gripping surface (16, 26) will come to bear on either side of the tissues at the time of stapling, to ensure holding thereof without perforating same.

The functioning of the staple is as follows: the staple is positioned against the two lips to be stapled with an applicator. The staple is in the open position and the two pointed ends (11, 21) fit flush with the tissues on either side of the separation line of the two lips. These pointed ends (11, 21) slightly penetrate the tissues and hook onto them in order to bring them together when the staple starts to be closed by an instrument folding the two arms (1, 2) with respect to the median axis passing through the tubular part of the transverse area (3). The pointed ends (11, 21) then make a sweeping movement in an arc of a circle, which brings the tissues at the edge of the lips between the two arms, between the two hooks (15, 25). When the two arms are folded against each other, the gripping surfaces (16, 26) hold the edges of the lips in position.

The functioning is as follows. The staple is in the open position before use, that is to say the arms are separated from each other. They may, in some embodiments, be aligned with each other so as to facilitate the introduction of the staple into the endoscope tube with a small cross section.

When the pointed ends (11, 21) come into contact with the tissue lips to be brought together, they penetrate the tissues very superficially, to form two anchoring points. When a force is applied to deform the staple and to bring the two arms (1, 2) together, these "anchorings" make it possible to drag the tissue lips in order to bring them together and to make the edges of the lips enter the opening form between the two arms (1, 2) of the staple. These edges are brought into the midplane of the staple and come into contact with the non-pointed semi-tubular surface (25, 26) of the two hooks (15, 25), which do not penetrate the tissues but exert a pressure in opposite directions and grip the tissues. When the arms (1, 2) are folded in a substantially parallel position with respect to each other, the gripping surfaces of the tissues are substantially parallel and exert a pressure perpendicular to the surface of the tissues, which holds the two edges of the tissues against each other.

Detailed Description of a Second Example Embodiment of a Staple

Figure 4:
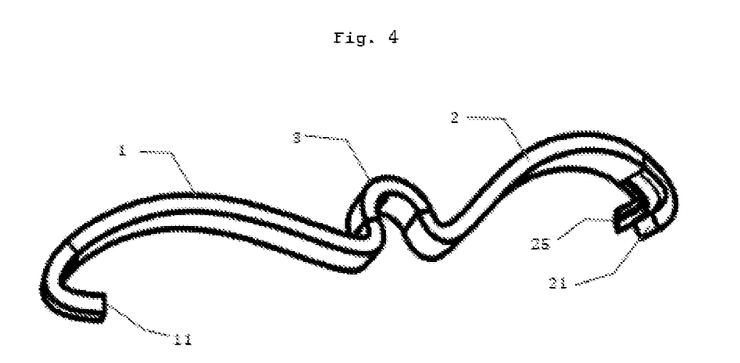
FIG. 4 shows a perspective view of a staple according to a second variant embodiment of the invention.
Figure 5:
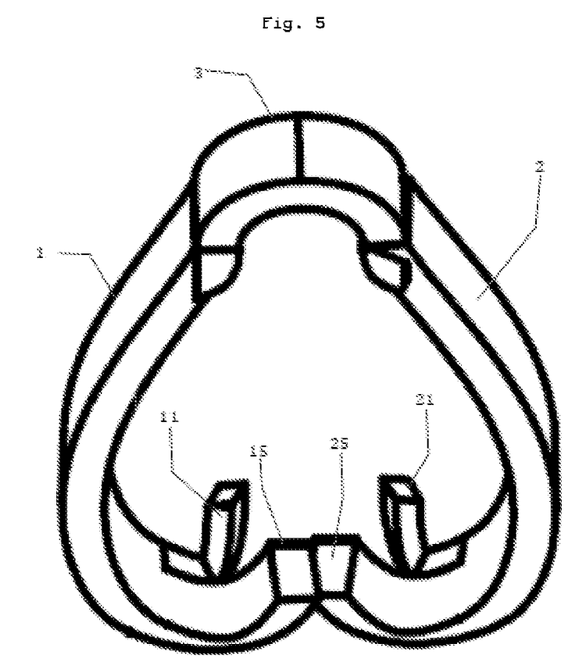
FIG. 5 shows a plan view of the staple in the closed position.

FIGS. 4 and 5 show another variant embodiment where the arms (1, 2) form a V, the opening of which decreases on opening. It can be produced by folding a metal rod in order to form two arched arms (1, 2) each terminating in a forked end defining an attachment end (11, 21) and a hook (15, 25) for gripping the tissues when the staple is closed.

Detailed Description of a Third Example Embodiment of a Staple

Figure 6:
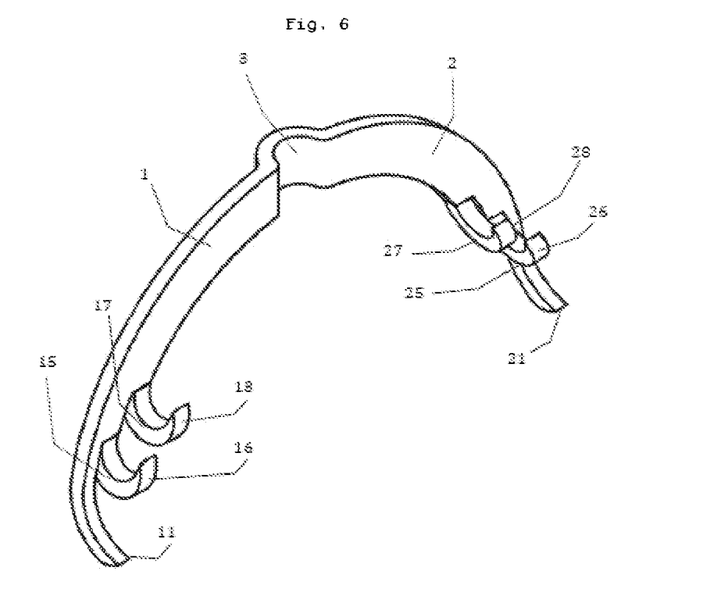
FIG. 6 shows a perspective view of a staple according to a third variant embodiment of the invention.
Figure 7:
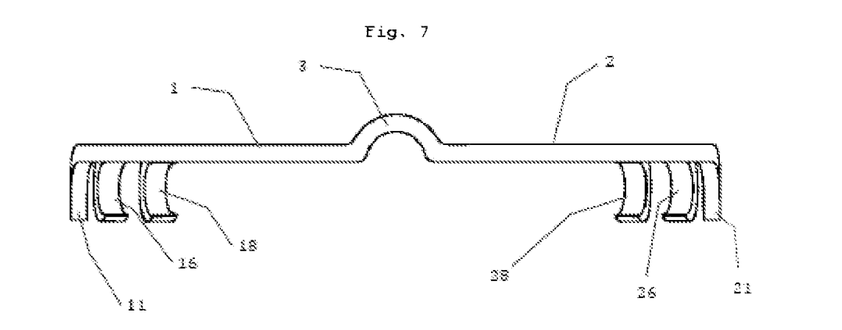
FIG. 7 shows a plan view of the staple in the open position.

FIGS. 6 and 7 show another variant embodiment where the arms (1, 2) carry a plurality of hooks (15, 17; 25, 27) each having a gripping surface (16, 18; 26, 28). This solution makes it possible to increase the gripping surface of the tissues.

Detailed Description of a Fourth Example Embodiment of a Staple

Figure 8:
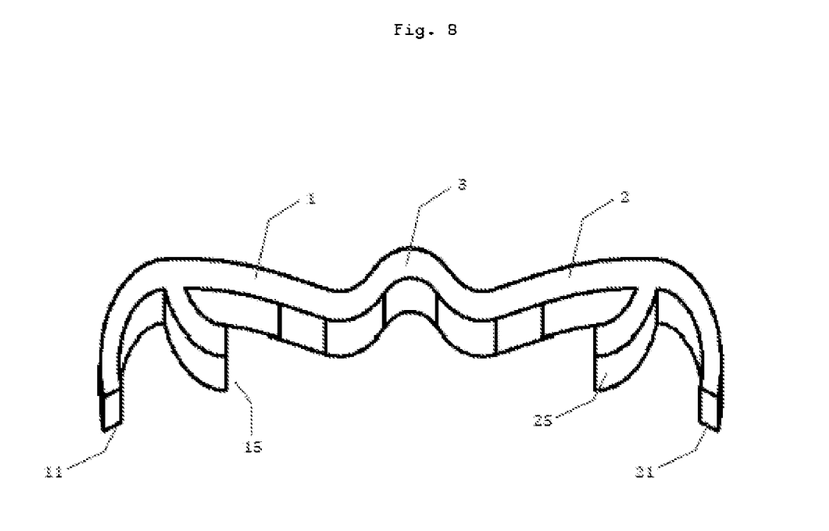
FIG. 8 shows a plan view of a fourth variant of a staple in the open position.

FIG. 8 shows another variant embodiment of a staple cut from a metal sheet by laser cutting or water-jet cutting. The direction of cut is either perpendicular to the plane of the metal sheet or inclined by an angle of between 10° and 55° that is constant throughout the path of the cutting, in order to form a staple having inclined faces facilitating loading onto the applicator. The staple has a constant thickness and a configuration having two arms (1, 2) extending on either side of a curved area, each arm (1, 2) having a first claw respectively (11, 21) and a hook respectively (15, 25).

Detailed Description of a First Example of an Applicator

Figure 9:
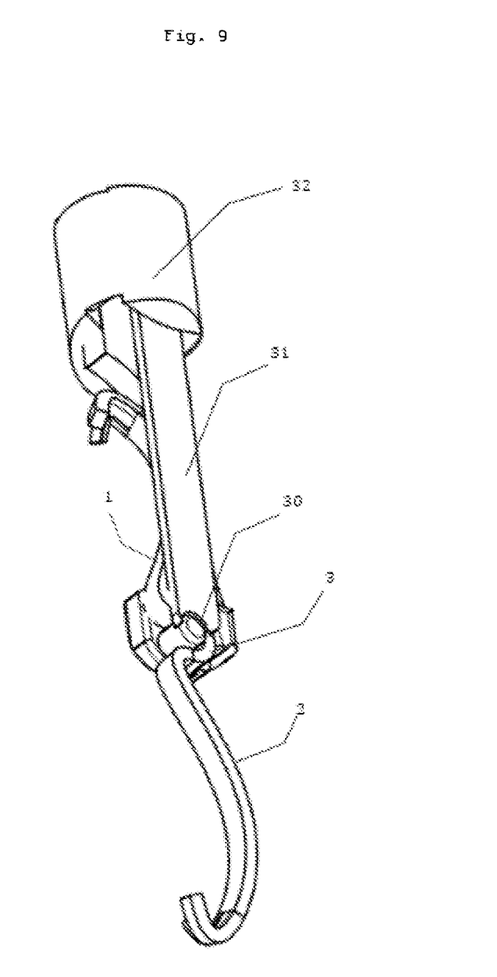
FIGS. 9 and 10 show views of an example of a staple applicator respectively during the phase of introducing the endoscope during the stapling phase.
Figure 10:
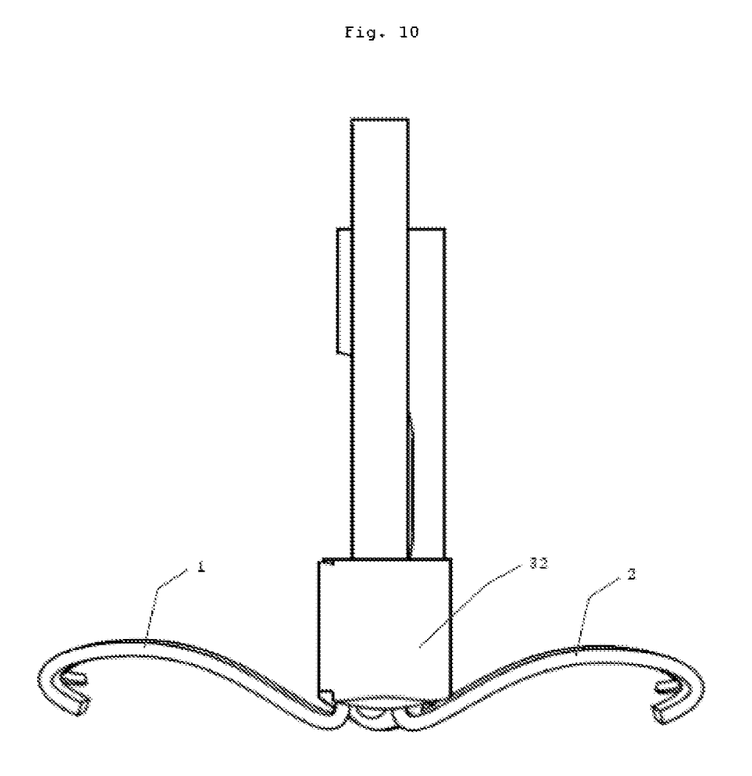

FIGS. 9 and 10 present a first example of an endoscope applicator, for a staple corresponding to the second example embodiment. In the position of introduction of the endoscope, the staple is oriented longitudinally, so that the two arms (1, 2) are aligned with the axis of the tubular end of the endoscope. The semicircular segment (3) extended on either side by the arms (1, 2) is positioned around a cylindrical lug (30) carried by a longitudinally movable rod (31) that is actuated by an external control member. When the staple is positioned, the operator pushes the rod (31) in order to make the whole of the staple emerge from the tubular sleeve (32) provided at the end of the endoscope. The following step consists of withdrawing the movable rod (31), which causes the tilting of the staple, the back of which comes into contact with the front surface of the tubular sleeve (32). The staple then comes to be positioned transversely, after having tilted at 90°, and the two arms (1, 2) come into contact with the front surface of the sleeve (32), as shown in FIG. 9. When traction is continued to be exerted on the control member of the rod (31), the deformation of the staple and the bringing together of the two arms (1, 2) are caused, and consequently the attachment of the tissues by the pointed ends (11, 21), and then gripping thereof by the hooks (15, 25).

Detailed Description of a Second Example of an Applicator

Figure 11:
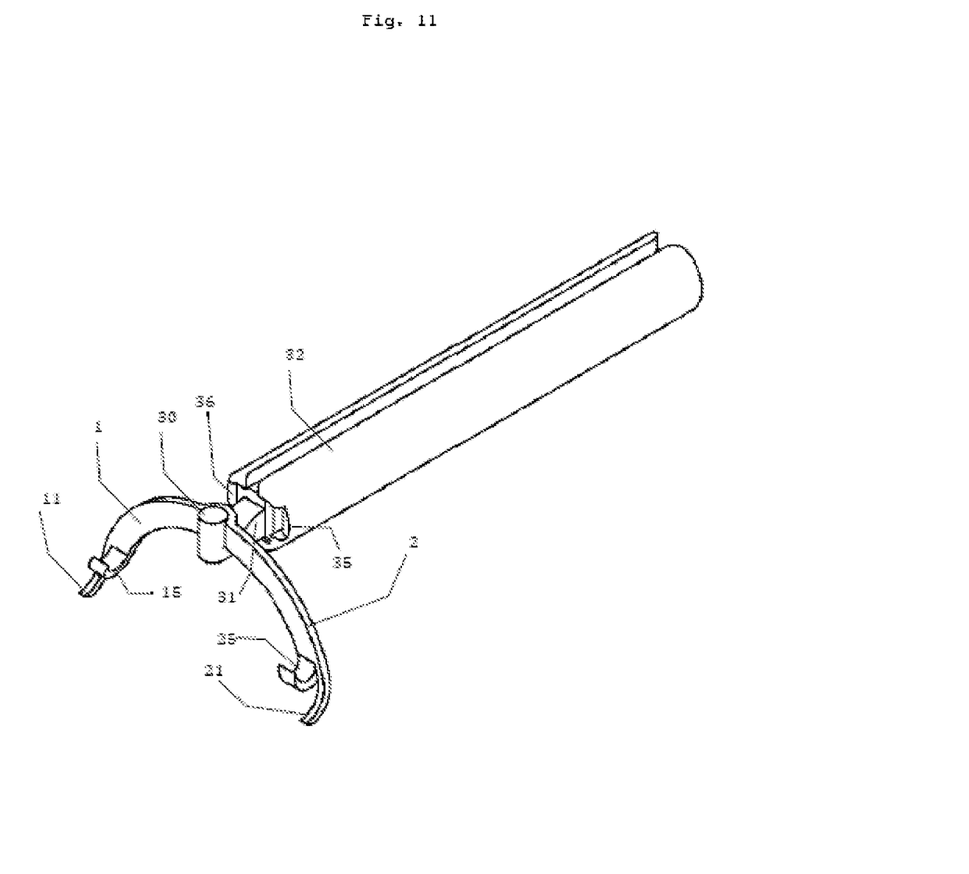
FIG. 11 shows a view of a second example of a staple applicator.

FIG. 11 shows another example embodiment of an applicator according to the invention. In this example, the staples are positioned transversely, the tubular part of the central area (3) being placed at the rear of a lug (30) supported by a transversely movable rod (31) that is actuated by an operator using an external manipulation member.

When the operator withdraws the rod (31) towards the rear, the lug (30) drives the staple until the rear surfaces of the arms (31, 32) come into contact with the front end of the tubular sleeve (32) provided at the end of the endoscope. This front end has two flats (35, 36) providing the wedging of the arms (1, 2) of the staple. By continuing the traction force, the staple is deformed and the two arms (1, 2) move closer together, which causes the attachment of the tissues by the claws (11, 21), and then the gripping of the tissues between the two hooks (15, 25).

Description of Another Staple/Applicator Assembly

Figure 12:
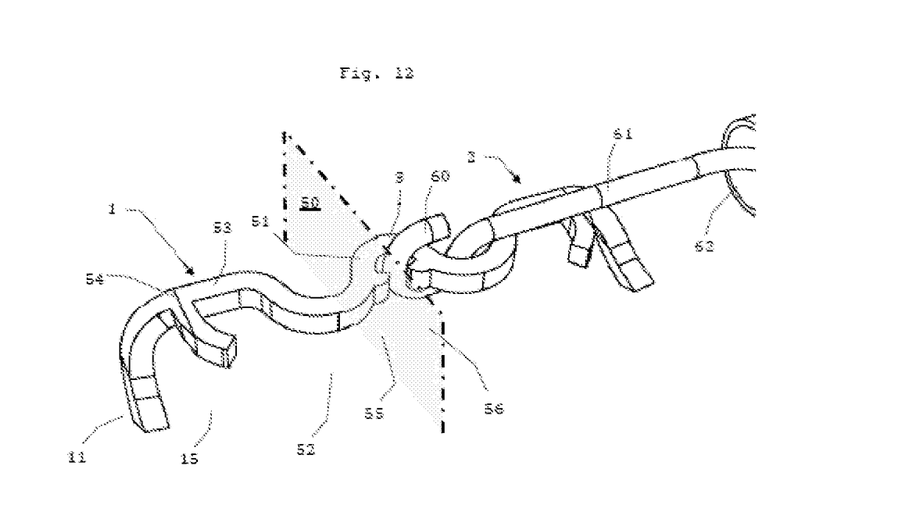
FIGS. 12 to 14 show views of another overall staple/applicator example.
Figure 13:
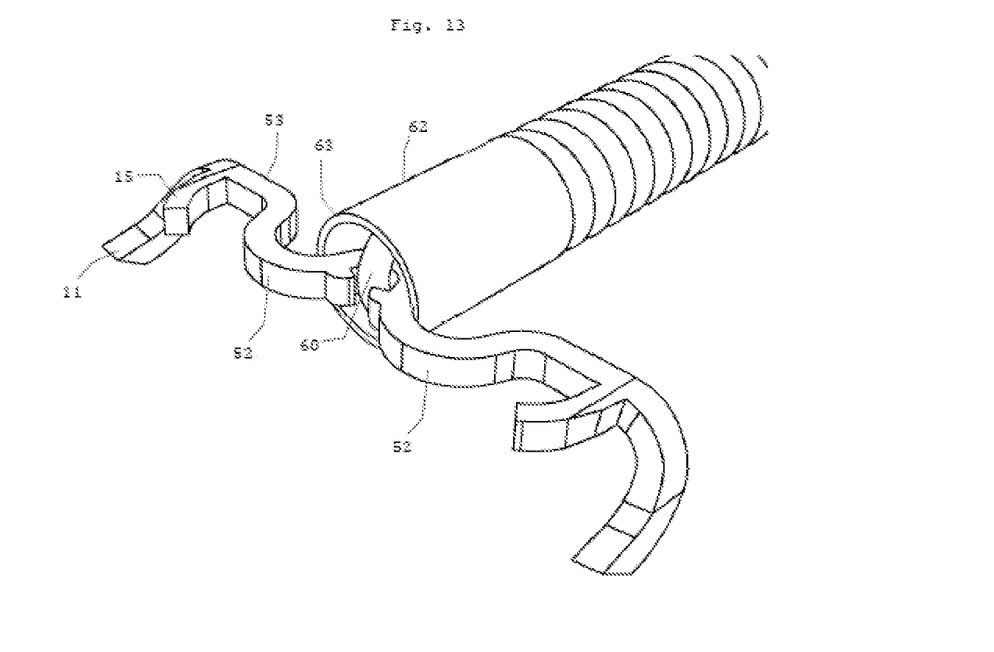
Figure 14:
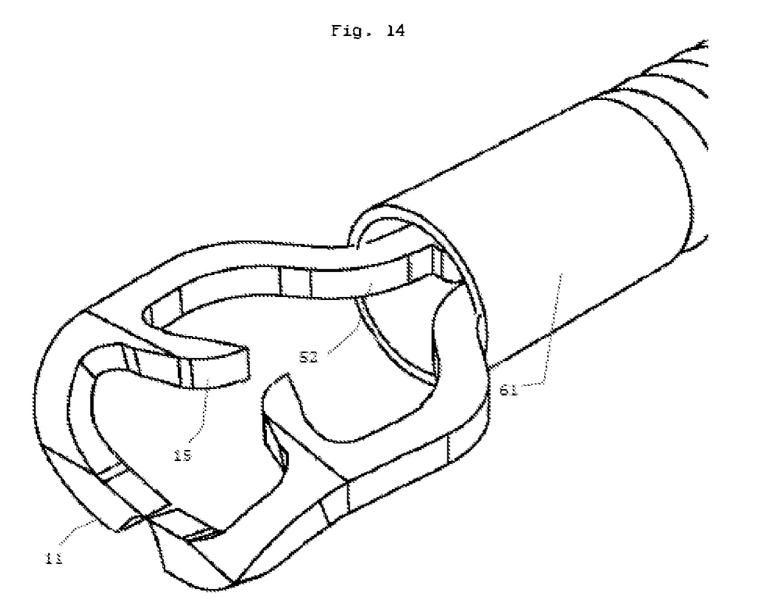

The staple has two arms (1, 2) that are aligned before positioning. The staple has, between these two arms (1, 2), a transverse connection area (3). This transverse connection area (3) is in the general form of a C, symmetrical with respect to the midplane (4) of the staple. This transverse connection area (3) has, on either side of the midplane, an arched portion (51) extending over an angle of preferably between 70° and 85° extended by a second arched portion (52) with an angle of curvature in the opposite direction extending over approximately 180°. This second arched portion (52) is itself extended by a third portion (53) perpendicular, before deformation, to the symmetry plane (4). This third portion (53) has a bifurcation (54) extended by a hook forming the gripping area (15, 25) on the one hand and by a second hook, the two hooks being curved towards the inside of the staple.

The transverse connection area (3) has notches (55, 56) partially enclosing the opening, so as to allow the engagement of a deformable hook (60) provided at the end of the applicator rod (61). To allow introduction into an endoscope tube (62), the staple is placed longitudinally, in an open position in which the two arms are aligned, one of the arms (2) being applied against the rod (61) and the other arm (1) being opposed, in line with the rod (61).

The applicator makes it possible to bring the staple to the positioning point. The rod (61) is then pushed in order to make the staple emerge from the end of the endoscope tube, which causes the tilting of the staple. By next withdrawing the rod (61), the hook (60) drives the transverse connection area (3) in the end piece of the endoscope tube (62), until the rear surface of the arms (2, 3), at the second section (52), comes to be locked against the front edge (63) of the end of the endoscope tube (62).

In continuing the traction on the rod (61), the second portion (52) deforms, which causes the ends of the arms to come together, and in particular the two hooks forming respectively the attachment areas (11) and the gripping areas (15, 25). When the staple is closed, the hook is unhooked, increasing the traction on the rod, which deforms the hook, which opens and disengages from the transverse connection area (3) of the staple. The invention relates to staples, and in particular staples having before use the form illustrated by FIG. 12, of applicators for endoscopic insertion and stapling, as well as systems comprising an applicator and suitable staples.

What is claimed is:

1. An applicator for a surgical staple, the applicator comprising:
    a tubular element,
    a movable member at least partially disposed within the tubular element and configured to be moved between a first position, a second position, a third position, and a fourth position,
        the movable member couplable to the staple,
        the staple including a first arm and a second arm connected by a transverse connection area, the movable member couplable to the transverse connection area,
        in the first position the movable member is configured to hold the staple so that a major axis of the staple is substantially parallel with a major axis of the movable member,
        in the second position the movable member is configured to hold the staple in so that the major axis of the staple is substantially perpendicular with the major axis of the movable member,
        in the third position the movable member is configured to hold the staple in a folded configuration where the first arm of the staple is substantially parallel with the second arm of the staple,
        in the third position the movable member is configured to apply a pressure to an exterior-facing surface of the staple such that the staple is moved to and held in the folded configuration, and
        in the fourth position the movable member is configured to disengage from the staple.

2. The applicator of claim 1, wherein the movable member includes a lug that is couplable to the staple.

3. The applicator of claim 1, wherein the first position is an extended position, and the third position is a retracted position.

4. The applicator of claim 1, wherein the tubular element is configured to surround at least a portion of the staple when the movable member is in the second position.

5. The applicator of claim 4, wherein the tubular element is configured to surround the transverse connection area when the movable member is in the second position.

6. The applicator of claim 1, wherein the movable member includes a deformable hook that interacts with an interior-facing surface of the transverse connection area.

7. The applicator of claim 6, wherein the transverse connection area includes an arched portion that is centered about a midplane of the staple and configured to receive the deformable hook.

8. The applicator of claim 1, wherein, in the second position, the staple is substantially perpendicular to a major axis of the tubular element and at least partially disposed within the tubular element.

9. The applicator of claim 1, wherein, in the second position, the first and second arms of the staple are in contact with the tubular element.

10. An applicator for a surgical staple, the applicator comprising:
    a tubular element,
    a movable member having a deformable hook and at least partially disposed within the tubular element,
        the staple including a first arm and a second arm connected by a transverse connection area,
        the movable member couplable to the transverse connection area,
        the deformable hook of the movable member configured to interact with an interior-facing surface of the transverse connection area,
        the movable member configured to be moved between a first position and a second position,
        in the first position the movable member is configured to hold the staple so that a major axis of the staple is substantially parallel with a major axis of the movable member, and
        in the second position the movable member is configured to hold the staple in so that the major axis of the staple is substantially perpendicular with the major axis of the movable member.

11. The applicator of claim 10, wherein the first position is an extended, and the second position is a retracted position.

12. The applicator of claim 10, wherein the movable member is further configured to be moved between the second position and a third position, in the third position the movable member is configured to hold the staple in a folded configuration where the first arm is substantially parallel with the second arm.

13. The applicator of claim 12, wherein, in the third position, the tubular element is configured to apply a pressure to an exterior-facing surface of the staple such that the staple is moved to and held in the folded configuration.

14. The applicator of claim 13, wherein the movable member is further configured to be moved between the third position and a fourth position, in the fourth position the movable member is configured to disengage from the staple.

15. The applicator of claim 12, wherein the tubular element is configured to surround at least a portion of the staple when the movable member is in the second position.

16. The applicator of claim 15, wherein the tubular element is configured to surround the transverse connection area when the movable member is in the second position.

17. An applicator for a surgical staple, the applicator comprising:
   a tubular element,
   a movable member at least partially disposed within the tubular element and configured to be moved between a first position, a second position, a third position, and a fourth position,
      in the first position the movable member is configured to hold the staple so that a major axis of the staple is substantially parallel with a major axis of the movable member,
      in the second position the movable member is configured to hold the staple in so that the major axis of the staple is substantially perpendicular with the major axis of the movable member,
      in the third position the movable member is configured to hold the staple in a folded configuration, where a first arm of the staple is substantially parallel with a second arm of the staple, and
      in the fourth position the movable member is configured to disengage from the staple.

18. The applicator of claim 17, wherein the first position is an extended position, and the third position is a retracted position.

19. The applicator of claim 17, wherein the tubular element is configured to surround at least a portion of the staple when the movable member is in the second position.

20. The applicator of claim 19, wherein the tubular element is configured to surround a transverse connection area of the staple when the movable member is in the second position.

21. The applicator of claim 20, wherein the movable member includes a deformable hook that interacts with an interior-facing surface of the transverse connection area.

* * * * *